United States Patent
Schwartz et al.

(10) Patent No.: US 8,222,294 B2
(45) Date of Patent: Jul. 17, 2012

(54) COMBINATIONS OF AN ANTI EMETIC AGENT AND AN ENKEPHALINASE INHIBITOR

(75) Inventors: Jean-Charles Schwartz, Paris (FR); Jeanne-Marie Lecomte, Paris (FR)

(73) Assignee: Bioproject, Paris (FR)

( * ) Notice: Subject to any disclaimer, the term of this patent is extended or adjusted under 35 U.S.C. 154(b) by 210 days.

(21) Appl. No.: 10/587,899

(22) PCT Filed: Feb. 14, 2005

(86) PCT No.: PCT/IB2005/000351
§ 371 (c)(1), (2), (4) Date: Apr. 27, 2007

(87) PCT Pub. No.: WO2005/079850
PCT Pub. Date: Sep. 1, 2005

(65) Prior Publication Data
US 2007/0275993 A1    Nov. 29, 2007

(30) Foreign Application Priority Data
Feb. 12, 2004  (EP) ..................................... 04290384

(51) Int. Cl.
*A61K 31/24* (2006.01)
*A61K 31/4178* (2006.01)
*A61K 31/439* (2006.01)

(52) U.S. Cl. ......... 514/538; 514/541; 514/305; 514/397

(58) Field of Classification Search ........................ None
See application file for complete search history.

(56) References Cited

U.S. PATENT DOCUMENTS
2004/0115258 A1* 6/2004 Stroppolo et al. ............ 424/465

OTHER PUBLICATIONS

Boige et al., Bulletin of Cancer, 88(2), 163-73 (Feb. 2001).*
Cojocaru et al., Archives Pediatr. (2002), 8: 774-9.*
Lecomte JM: "An overview of clinical studies with raccadiotril in adults", Int'l Journal of Antimicrobial Agents, vol. 14, No. 1 Feb. 2000—pp. 781-787.
Baumer P. et al.: "Symptoatic treatment of adult acute diarrhea . . . , Clinical equivalence of (R)-Acetorphan and . . . ", Gastroenterology, vol. 116, No. 4, part 2—Apr. 1999, p. A859.
Farthing MJ: "Introduction. Enkephalinase inhibition: a rational approach to antisecretory therapy for . . . ", Alimentary Phar. & Therapeutics, Dec. 1999, vol. 13, suppl 6,—pp. 1-2.
Primi MP et al: "Racecadotril demonstrates intestinal antisecretory activity in vivo.", Alimentary Pharm. & Therapeutics, Dec. 1999, vol. 13, suppl 6, pp. 3-7.
Turvil JL et al: "Effect of granisetron on cholera toxin-induced enteric secretion . . . ", Lancet 1997 UK, vol. 349, No. 09061, p. 1293.
Cubeddu LX et al: "Antiemetic activity of ondansetron in acute gastroenteritis", Alimentary Pharm. and Therapeutics, vol. 11, No. 1, 1997, pp. 185-191.
Ramsook et al.: "A randomized clinical trial comparing oral ondasetron with placebo in . . . ", Annals of Emergency Medicine, Apr. 2002, vol. 39, No. 4—pp. 397-403.
Farthing MJG: "Diarrhoea" A significant worldwide problem, Int'l Journal of Antimicrobial Agents, vol. 14, No. 1, Feb. 2000—pp. 65-69.
Blandizzi et al: "Characterization of a novel mechanism accounting for the adverse cholinergic effects of the anticancer drug irinotecan", British HJournal of Pharmacology, vol. 132, no. Jan. 2001—pp. 73-84.
Pizzolato JF et al: "The camptothecins", The Lancet, Lancet Ltd., London, GB, vol. 361, No. 9376, Jun. 28, 2003, pp. 2235-2242.

* cited by examiner

*Primary Examiner* — Phyllis G. Spivack
(74) *Attorney, Agent, or Firm* — B. Aaron Schulman, Esq.; Stites & Harbison PLLC

(57) ABSTRACT

The present invention concerns combinations of an anti-emetic agent and an enkephalinase inhibitor for use in methods for treating diarrhea and/or gastroenteritis.

20 Claims, No Drawings

COMBINATIONS OF AN ANTI EMETIC AGENT AND AN ENKEPHALINASE INHIBITOR

Gastroenteritis is a disease of infectious origin caused by a variety of bacteria, virus or parasites.

It manifests itself essentially by diarrhoea (i.e. net intestinal hypersecretion of water and electrolytes), nausea, vomiting and abdominal pain. Among these manifestations, those leading to fluid and electrolyte losses, i.e. vomiting and diarrhoea, are particularly dangerous in young children in which dehydration, a life-threatening manifestation, may result.

For a long time, this infectious disease was cured by the use of opiates (or opiate-like drugs), anti-infective agents and oral rehydration solutions but each of these treatments suffers from drawbacks. Thus opiates tend to enhance bacterial infection and nausea, induce vomiting and reactive constipation and display potential CNS toxicity in infants; anti-infective are only active against a small fraction of the causal agents; rehydration solutions, although highly recommended in infants, do not shorten the duration of the disease and tend to augment nausea and vomiting. Sometimes, dopamine antagonists with a predominant peripheral action, e.g. domperidone or metoclopramide, are associated with the antidiarrheal treatments in order to prevent nausea and vomiting but such agents may cause extrapyramidal symptoms. More recently, two novel classes of drugs were experienced for alleviating the various manifestations of gastroenteritis: enkephalinase, i.e. neprilysin (NEP) inhibitors, e.g. racecadotril or dexecadotril, which inhibit the net intestinal hypersecretion of water and minerals (reviewed in Lecomte, *Int. J. of Microbial Agents* 2000, 14, 81) and 5-HT$_3$ receptor antagonists which prevent emesis associated with serotonin release from the gastrointestinal tract occurring in gastroenteritis (Cubeddu et al., *Aliment. Pharmacol. Ther.,* 1997, 11, 189; Ramsook et al., *Ann. Emerg. Med.,* 2002, 39, 397; Reeves et al., *Pediatrics,* 2002, 109, e 62).

However, while each of these two classes of agents is able to prevent some symptoms of gastroenteritis, they are unable to prevent their totality.

Hence NEP inhibitors do not prevent nausea and vomiting which may result in drug and hydroelectrolyte losses and limits treatment compliance. On the other hand, 5-HT$_3$ receptor antagonists are currently not approved in gastroenteritis in spite of their anti-emetic efficacy since they were not reported to limit hydroelectrolytic losses via diarrheic stools and one of these agents, ondansetron, was shown either to fail to affect diarrhoea (Reeves et al., op. cit.) or even increase its duration (Ramshook et al., op. cit.). In fact, diarrhoea has even been described as a side effect resulting from treatment of gastroenteritis by ondansetron (Cubeddu et al., *Alimentary Pharmacology and Therapeutics,* 1997, 11 (1), 18(-191).

Thus, there has been a prejudice against using 5-HT$_3$ receptor antagonists in patients suffering with diarrhoea such as patients with gastroenteritis. As a result, the use of a 5-HT$_3$ receptor antagonist in combination with a NEP inhibitor has neither been disclosed nor suggested or envisaged.

The present inventors have now unexpectedly found that such a combination greatly improves the treatment of gastroenteritis.

More precisely, it has been found that the association of a 5-HT$_3$ receptor antagonist, such as ondansetron or granisetron, and an enkephalinase inhibitor, such as racecadotril or dexecadotril, realizes an unexpected synergy. Accordingly, said combination allows to suppress main or all manifestations of acute gastroenteritis.

Without to be bound by any theory, the following unexpected advantages of the combination of the present invention have been identified by the present inventors:

1) The combinations of the invention exhibit activity for a broader germ spectrum and involve complementary mechanisms.

Net intestinal hydroelectrolytic hypersecretion is partially inhibited by both types of agents; this effect involves distinct neural mechanisms and, therefore, allows a synergy when both are used together.

In agreement, serotonin, via its 5-HT$_3$ receptors, exerts a pro-secretory effect whereas enkephalins (when protected against degradation by enkephalinase inhibitors), exert an opposite effect via their delta receptor (Shooketal., *J.P.E.T.* 1989, 249, 83).

Furthermore, the intestinal antisecretory activity of the two classes of agents is elicited differently against the presumably diverse causal germs as a consequence of different neural pathways involved in their pro-secretory action. Thus, ondansetron prevents the hypersecretion elicited by *Salmonella* but not cholera or *E. coli* toxins (Grodahl et al., *J. Med. Microbiol.* 1998, 47, 151; Rolfe et al., *J. Physiol.* 1992, 446, 1078) whereas enkephalinase inhibitors, e.g. racecadotril or dexecadotril, are active against cholera and *E. coli* toxins (Primi et al., *Dig. Dis. Sci.* 1986, 31, 172; Banks, Bose, Farthing, *The effects of enkephalinase inhibitor racecadotril on enterotoxin-induced intestinal secretion in rat*. Submitted).

Enkephalinase inhibitors exert at low dose (e.g. dexecadotril 0.1 mg/kg) an antidiarrheal activity, as assessed in various experimental models, such as castor oil and L.P.S. typhimurium-induced diarrhoeas. Unexpectedly, the combination according to the invention for instance association of dexecadotril 0.1 mg/kg with ondansetron 1 mg/kg) strongly potentiate (p<0.01) antidiarrheal activity and completely prevented diarrhoea.

Acute gastroenteritis often involves several germs and, in any event, treatment should be started before any microbiological diagnostic. Thus, the combination of the present invention makes it possible to systematically associate two drugs with antisecretory activity elicited against different germs and via distinct mechanisms.

2) The combinations of the invention allow inhibition of the major manifestations of gastroenteritis.

Emesis, a cardinal manifestation of gastroenteritis, particularly in children, is significantly reduced by 5-HT$_3$ antagonists as shown in the case of ondansetron (Cubeddu et al, op. cit.; Reeves et al., op. cit.) although diarrhoea was not significantly affected or even increased.

In contrast, various clinical trials have shown that enkephalinase inhibitors do not reduce this manifestation in spite of their antidiarrheal efficacy (reviewed in Lecomte, op. cit.).

Unexpectedly, however, the inventors have found that the combination of an enkephalinase inhibitor with a 5-HT$_3$ antagonist potentiates the antiemetic effect of 5-HT$_3$ antagonist. In particular the inventors demonstrated that dexecadotril in low dosage (0.1 mg/kg p.o.) potentiates the antiemetic effect of ondansetron (1 mg/kg) in a classical animal model of emesis i.e. cisplatin-induced emesis in the ferret. The combinations of the present invention thus allow systematic association of the two classes of agents to block the two major manifestations of the disease and prevent hydroelectrolytic losses occurring at the two ends of the gastrointestinal tract.

3) The combinations of the invention greatly optimize the administration of enkephalinase inhibitors administered alone.

Administration of a combination of the present invention comprising an antiemetic agent together with an enkephalinase inhibitor enhances the bioavailability of the latter by preventing its expulsion through vomiting. Association of racecadotril with oral rehydration solutions is a proven beneficial therapeutic strategy in gastroenteritis (Lecomte, op. cit.) but administration of these solutions tends to enhance vomiting, thus reducing the efficacy of the treatment and sometimes leads even to hospitalization and intravenous rehydration (Inserman et Lemg, Can. Fam. Physician 1993, 39, 2129). Hence, administration of a combination of the present invention provides a synergistic effect and facilitates the administration of oral rehydration solutions in addition to enkephalinase inhibitors.

4) The combinations of the invention significantly improve the action of enkephalinase inhibitors administered alone.

Transit through the human colon is delayed by administration of 5-HT$_3$ antagonists (Gore et al., Aliment. Pharmacol. Ther., 1990, 4, 139) Enkephalinase inhibitors do not appear to delay the ileocaecal transit (Bergmann et al., Aliment. Pharmacol. Ther. 1992, 6, 305). However the authors of the present invention have found that racecadotril and, to a lesser extent dexecadotril, tend to accelerate colonic transit in rodents. This effect is blocked by co-administration of ondansetron. Since the transit is already strongly accelerated in gastroenteritis, the combinations of the present invention allow the antisecretory pro-absorptive activity of enkephalinase inhibitors to be exerted for a longer time upon the watery intestinal lumen content, thus resulting in a synergic antidiarrheal effect.

5) The combinations of the invention exhibit a synergetic effect against abdominal pain.

Abdominal pain is one general manifestation of gastroenteritis. It is significantly diminished by treatment with enkephalinase inhibitors such as racecadotril (Lecomte, op. cit.). This drug exerts partial antinociceptive effect via protection of endogenous opioid peptides in the rodent model of abdominal cramps (Lecomte et al., J.P.E.T. 1986, 237, 937). On the same rodent model, 5-HT$_3$ antagonists also partially prevent visceral pain manifestations by an obviously different neural mechanism (Veevanpaneyulu et al., Pharm. Pharmacol. Communic. 2000, 6, 513).

The combinations of the invention involve a synergy against abdominal pain as the authors of the present invention have discovered using a classical model of abdominal pain in rodents (Morteau et al., Gastroenterology, 1993, 104, 47). Rats were preteated with trinitrobenzenesulfonic acid to induce intestinal inflammation and pain sensitivity, as assessed by evaluation of the abdominal cramps elicited by rectal distention. 5HT$_3$ antagonists (in particular ondansetron) and enkephalinase inhibitors (in particular racecadotril or dexecadotril) partially prevent these pain manifestations when administered alone but completely prevent them when the two classes of compounds are combined.

Hence there is a clear synergy regarding visceral pain, a major symptom in gastroenteritis.

6) The combinations of the invention exhibit optimized pharmacokinetics.

Pharmacokinetics and drug metabolism data of enkephalinase inhibitors, such as racecadotril (or dexecadotril) and 5-HT$_3$ receptor antagonists such as ondansetron appear compatible with a co-administration of the two classes of drugs.

Typically, racecadotril displays a plasma half-life of $\cong 3$ hours and is administered three times a day.

Typically, ondansetron (and granisetron) displays a plasma half-life of ~3 hours and is also administered three times per day.

Therefore, according to a preferred aspect of the invention, the combinations of the invention are administered in the same dosage form (capsule, table, powder, etc.).

The metabolism of 5-HT$_3$ receptor inhibitors such as ondansetron (or granisetron) involves oxidation by various cytochrome P 450 subtypes whereas the inventors have found that enkephalinase inhibitors, such as racecadotril (and dexecadotril) and their active metabolites, do not significantly interact with cytochrome P 450 subtypes and their metabolism mainly occurs via S-methylation. Thus, this results in the limited metabolic interaction of the two classes of drugs present in the combinations of the invention.

7) The inventors have found that the combinations of the present invention are well tolerated and animal data indicate that their association is non toxic.

Thus, according to a first object, the present invention provides combinations of an antiemetic agent with an enkephalinase inhibitor. According to a preferred aspect, said antiemetic agent is a 5-HT$_3$ receptor antagonist. According to a still preferred aspect, said 5-HT$_3$ receptor antagonist is chosen from the list consisting in ondansetron or granisetron.

According to another preferred aspect, said enkephalinase inhibitor is chosen from the list consisting in racecadotril or dexecadotril.

According to a second object, the present invention provides a pharmaceutical composition comprising a combination according to the present invention as discussed above, with a pharmaceutically acceptable vehicle or excipient.

According to a preferred aspect, said pharmaceutical composition is for simultaneous, separate and sequential administration of its active ingredients.

According to a still preferred aspect, said pharmaceutical composition is suitable for oral administration.

According to an advantageous aspect, preferred combinations are those that exhibit a synergistic effect.

According to another preferred aspect, said pharmaceutical composition is in the form of tablets, dragees, powders, elixirs, syrups, liquid preparations, including suspensions, sprays, lozenges, emulsions, solutions, granules, capsules, more preferably tablets, capsules or granulated powder.

According to another preferred aspect, the pharmaceutical composition of the invention comprises between 50 and 100 mg of said enkephalinase inhibitor per dosage unit for adults and corresponding doses for children or babies according to their body weights.

According to another preferred aspect, said pharmaceutical composition comprises between 1 and 8 mg of 5-HT$_3$ antagonist per dosage unit for adults and corresponding doses according to body weight for children and babies.

According to a still preferred aspect, said composition comprises between 2 and 8 mg of ondansetron per dosage unit for adults and corresponding doses according to body weight for children and babies.

According to another still preferred aspect, pharmaceutical composition of the invention comprises between 1 and 4 mg of granisetron per dosage unit.

According to a still preferred aspect, said pharmaceutical composition comprises the combination of the invention in the same dosage unit.

According to another object, the present invention provides the use of the combination of the invention in the preparation of a pharmaceutical composition according to the invention for the treatment of acute gastroenteritis.

According to a preferred aspect, the present invention provides the use of the combination of the invention in the preparation of a pharmaceutical composition according to the invention for the treatment of acute diarrhoea associated with emesis.

According to a still preferred aspect, said diarrhoea is chemotherapy-induced diarrhoea, carcinoid diarrhoea, traveller's diarrhoea, diarrhoea elicited by various bacteria, viruses or parasites in adults, children or babies.

According to another preferred aspect, said treatment comprises oral administration, preferably two to four times a day.

According to particularly advantageous object, the present invention provides combinations of racecadotril and ondansetron.

According to a further advantageous object, the present invention provides pharmaceutical compositions comprising racecadotril and ondansetron, preferably for simultaneous, separate or sequential administration.

According to a still further advantageous object, the present invention provides the use of racecadotril and ondansetron for the preparation of a pharmaceutical composition for treating acute gastroenteritis or diarrhoea associated with emesis.

According to particularly advantageous object, the present invention provides combinations of dexecadotril and ondansetron.

According to a further advantageous object, the present invention provides pharmaceutical compositions comprising dexecadotril and ondansetron, preferably for simultaneous, separate or sequential administration.

According to a still further advantageous object, the present invention provides the use of dexecadotril and ondansetron for the preparation of a pharmaceutical composition for treating acute gastroenteritis or diarrhoea associated with emesis.

The preferred embodiments discussed herein above and/or herein below are to be understood on a separate basis or in combination with one another.

According to the present invention, pharmaceutical composition means a composition comprising one or more active ingredient as discussed above and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, dicalcium phosphate. Examples of disintegrating agents include starch, alginic acids and certain complex silicates. Examples of lubricants include magnesium stearate, sodium lauryl sulphate, talc, as well as high molecular weight polyethylene glycols.

Pharmaceutically acceptable means that it is, within the scope of sound medical judgment, suitable for use in contact with the cells of humans and lower animals without undue toxicity, irritation, allergic response and the like, and are commensurate with a reasonable benefit/risk ratio.

Representative dosage of the pharmaceutical compositions of the invention includes for example, tablets, dragees, powders, elixirs, syrups, liquid preparations, including suspensions, sprays, inhalants, lozenges, emulsions, solutions, granules, capsules and suppositories, as well as liquid preparations for injections, including liposome preparations, tablets, dragees, powders, elixirs, syrups, liquid preparations, including suspensions, sprays, lozenges, emulsions, solutions, granules, capsules, more preferably tablets, capsules or granulated powder. Techniques and formulations generally may be found in *Remington's Pharmaceutical Sciences*, Mack Publishing Co., Easton, Pa., latest edition.

Preferred formulations include tablets, dragees, powders, elixirs, syrups, liquid preparations, including suspensions, sprays, inhalants, lozenges, emulsions, solutions, granules, capsules, more preferably tablets, capsules or granulated powder.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used, they can contain emulsifying agents or agents which facilitate suspension. Diluents such as sucrose, ethanol, polyethylene glycol, propylene glycol, glycerol and chloroform or mixtures thereof may also be used.

Pediatric formulations e.g. powders, granulated powders, syrups or suspensions could be prepared using namely saccharose as a diluent, adjuvants and suitable taste-masking agents.

Solid compositions may also be employed as fillers in soft and hard-filled gelatin capsules using such excipients as lactose or milk sugar, as well as high molecular weight polyethylene glycols, and the like.

The pharmaceutical compositions can be administered in a suitable formulation to humans and animals by topical or systemic administration, including oral, inhalational, rectal, nasal, buccal, sublingual, parenteral (including subcutaneous, intramuscular, intravenous). It will be appreciated that the preferred route may vary with, for example, the condition of the recipient.

Preferably, the pharmaceutical compositions of the invention are suitable for oral administration to adults, children and babies.

According to the present invention, a pharmaceutical composition suitable for oral administration means a pharmaceutical composition which is in a form suitable to be administered orally to a patient. The composition may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

The compositions can be prepared in unit dosage form by any of the methods well known in the art of pharmacy. Such methods include the step of bringing into association the active ingredient with the carrier which constitutes one or more accessory ingredients. In general the compositions are prepared by uniformly and intimately bringing into association the active ingredient with liquid carriers or finely divided solid carriers or both, and then, if necessary, shaping the product.

A tablet may be made by compression or moulding, optionally with one or more accessory ingredients. Compressed tables may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compounds moistened with an inert liquid diluent. The tablets may optionally be coated or scored and may be formulated so as to provide slow or controlled release of the active ingredient therein.

Acid additional salts are formed with the active ingredients of the invention in which a basic function such as an amino, alkylamino, or dialkylamino group is present. The pharmaceutically acceptable, i.e., nontoxic, acid addition salts are preferred. The salts chosen are chosen optimally to be compatible with the customary pharmaceutical vehicles and adapted for oral or parenteral administration. Acid addition salts of the compounds useful according to this invention may be prepared by reaction of the free base with the appropriate acid, by the application or adaptation of known methods. For example, the acid addition salts of the compounds useful according to this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution. Some suitable acids for use in the preparation of such salts are hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic acid, malic acid, methanesulfonic acid, toluenesulfonic acid, fatty acids, adipate, alginate, ascorbate, aspartate, benzenesulfonate, benzoate, cyclopentanepropionate, digluconate, dodecylsulfate, bisulfate, butyrate, lactate, laurate, lauryl sulfate, malate, hydroiodide, 2-hydroxy-ethanesulfonate, glycerophosphate, picrate, pivalate, pamoate, pectinate, persulfate, 3-phenylpropionate, thiocyanate, 2-naphthalenesulfonate, undecanoate, nicotinate, hemisulfate, heptonate, hexanoate, camphorate, camphersulfonate, and others.

The acid addition salts of the active ingredients of the invention can be regenerated from the salts by the application or adaptation of known methods. For example, parent compounds useful according to the invention can be regenerated from their acid addition salts by treatment with an alkali, e.g. aqueous sodium bicarbonate solution or aqueous ammonia solution.

The active ingredients of the invention can be regenerated from their base addition salts by the application or adaptation of known methods. For example, parent compounds useful according to the invention can be regenerated from their base addition salts by treatment with an acid, e.g. hydrochloric acid.

Base addition salts may be formed where the compound useful according to the invention contains a carboxy group, or a sufficiently acidic bioisostere. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetra-methylammonium hydroxide, and the like.

The active ingredients of the invention may be conveniently prepared, or formed during the process of the invention, as solvates (e.g. hydrates). Hydrates of the active ingredients of the present invention may be conveniently prepared by recrystallisation from an aqueous/organic solvent mixture, using organic solvents such as dioxan, tetrahydrofuran or methanol.

According to the present invention, "synergistic" refers to the ability of the combination of the active ingredients of the present invention to achieve an effect that is not exerted by any of the active ingredients on its own, or to improve the effect obtained with each of the active ingredients on its own or the added effect of each active ingredient.

More preferably, "synergistic" refers to the ability of the combination of the present invention to achieve an effect superior to the added effect of each active ingredient.

Effect includes biological activity, advantageous pharmacodynamics or properties, or reduction of side effects.

The following example is given as a representative and non limitative aspect of the invention.

EXAMPLE

In Vivo Activity of the Combinations of the Invention

The outstanding activity of the combinations of the invention was evidenced on an animal model of experimental diarrhoea. A combination of the invention was evaluated on the castor oil-induced diarrhoea in rats, according to Niemegeers et al. (*Armeim.-Forsch.* (*Drug Res*), 1974, 24 No. 10).

Rats received ondansetron (0.1 mg/kg, p.o.) and racecadotril (40 mg/kg, p.o.) administered together. This combination elicited a nearly complete antidiarrheal effect for 6-7 h.

As comparative examples, ondansetron and racecadotril were also administered alone at the same dosages.

Ondansetron (0.1 mg/kg, p.o.) was found inactive on this model when administered alone.

Racecadotril (40 mg/kg, p.o.) administered alone induced a partial protection for 4 h on this model.

Furthermore, ondansetron at 1 mg/kg was also found inactive on this model but, when associated with 0.1 mg/kg dexecadotril, completely prevented the occurrence of diarrhoea on this model (whereas dexecadotril alone was only partially inactive).

Consequently, the combination of both classes of active agents elicited an activity clearly superior to the added activity of each active agent administered alone. The combinations of the invention thus exhibit a synergistic effect.

The invention claimed is:

1. A combination consisting essentially of racecadotril or dexecadotril with ondansetron or granisetron.

2. A pharmaceutical composition consisting essentially of the combination according to claim 1, and a pharmaceutically acceptable vehicle or excipient.

3. The combination according to claim 1, wherein said combination is for simultaneous, separate or sequential administration of racecadotril or dexecadotril and ondansetron or granisetron.

4. The pharmaceutical composition according to claim 2, wherein said pharmaceutical composition is suitable for oral administration.

5. The pharmaceutical composition according to claim 2, wherein said pharmaceutical composition is in the form of tablets, capsules or granulated powder.

6. The pharmaceutical composition according to claim 2, wherein the amount of racecadotril or dexecadotril per dosage unit for adults is from 50 to 100 mg.

7. The pharmaceutical composition according to claim 2 wherein the amount of ondansetron or granisetron per dosage unit for adults is from 1 to 8 mg.

8. The pharmaceutical composition according to claim 2 wherein the amount of ondansetron per dosage unit for adults is from 2 to 8 mg.

9. The pharmaceutical composition according to claim 2, wherein the amount of granisetron per dosage unit for adults is from 1 to 4 mg.

10. The pharmaceutical composition according to claim 2, wherein racecadotril or dexecadotril and ondansetron or granisetron are in the same dosage unit.

11. The pharmaceutical composition of claim 2, consisting essentially of racecadotril or dexecadotril suitable for oral administration, and ondansetron or granisetron suitable for oral administration.

12. A method for the treatment of acute gastroenteritis, consisting essentially of administering the combination of claim 1.

13. The method according to claim 12, wherein said treatment is administered orally.

14. The method according to claim 13, wherein said treatment is administered two to four times a day.

15. The method according to claim 12, wherein said combination is administered two to four times a day.

16. The method according to claim 12, wherein said combination consists essentially of dexecadotril and ondansetron for the treatment of acute gastroenteritis by simultaneous, separate or sequential oral administration of the active ingredients.

17. A method for the treatment of acute diarrhea associated with emesis, consisting essentially of administering the combination of claim 1.

18. The method according to claim 17, wherein said diarrhea is chemotherapy-induced diarrhea, carcinoid diarrhea, traveller's diarrhea, diarrhea elicited by various bacteria, viruses or parasites.

19. The combination of claim 1, consisting essentially of racecadotril and ondansetron.

20. The combination of claim 1, consisting essentially of racecadotril and granisetron.

* * * * *

UNITED STATES PATENT AND TRADEMARK OFFICE
CERTIFICATE OF CORRECTION

PATENT NO. : 8,222,294 B2
APPLICATION NO. : 10/587899
DATED : July 17, 2012
INVENTOR(S) : Schwartz et al.

Page 1 of 1

It is certified that error appears in the above-identified patent and that said Letters Patent is hereby corrected as shown below:

Title Page

At Item (73) Assignee please change:

"BIOPROJECT, Paris (FR)" to -- BIOPROJET, Paris (FR) --

Signed and Sealed this
Fourteenth Day of May, 2013

Teresa Stanek Rea
*Acting Director of the United States Patent and Trademark Office*